United States Patent [19]

Abrahamson

[11] Patent Number: 5,617,235
[45] Date of Patent: Apr. 1, 1997

[54] DEVICE FOR OPTICALLY TRANSMITTING AND RECEIVING BINARY INFORMATION

[75] Inventor: Hans Abrahamson, Stockholm, Sweden

[73] Assignee: Pacesetter AB, Solna, Sweden

[21] Appl. No.: 631,956

[22] Filed: Apr. 15, 1996

Related U.S. Application Data

[63] Continuation of Ser. No. 401,236, Mar. 9, 1995, abandoned.

[30] Foreign Application Priority Data

Mar. 10, 1994 [SE] Sweden .................................. 9400824

[51] Int. Cl.$^6$ ...................................................... H04B 10/00
[52] U.S. Cl. ........................... 359/142; 359/154; 359/172; 375/310
[58] Field of Search ..................................... 375/309, 310, 375/276, 259; 178/79–80, 89, 118

[56] References Cited

U.S. PATENT DOCUMENTS

| | | | |
|---|---|---|---|
| 4,628,541 | 12/1986 | Beavers | 359/142 |
| 4,850,046 | 7/1989 | Philippe | 359/142 |
| 5,319,487 | 6/1994 | Sato et al. | 359/142 |

FOREIGN PATENT DOCUMENTS

| | | |
|---|---|---|
| 0585030 | 3/1994 | European Pat. Off. . |
| 2228595 | 2/1989 | United Kingdom . |

*Primary Examiner*—Leo Boudreau
*Assistant Examiner*—Bhavesh Mehta
*Attorney, Agent, or Firm*—Hill, Steadman & Simpson

[57] ABSTRACT

A device for transmitting binary information, in the form of two information-carrying symbols, between two or a number of units, in which transmission is by optical means in free medium, includes an optical transmitter module with a transmitter unit for transmitting an optical transmission signal and an optical receiver module with a receiver unit for receiving the optical transmission signal, and the device is arranged for high speed communications without a carrier wave. The transmitter module is equipped with a formatting unit devised to activate the transmitter unit to emit the transmission signal only during part of a complete symbol interval corresponding to one of the symbols, and the receiver module is equipped with a normalizing unit devised to recreate, from the transmission signal received by the receiver unit, both the symbol corresponding to the transmission signal throughout its entire symbol interval and the residual information-carrying symbol in the digital information. A programmer and base unit for a medical implant in which the device for transmitting digital information is applied is also disclosed.

9 Claims, 2 Drawing Sheets

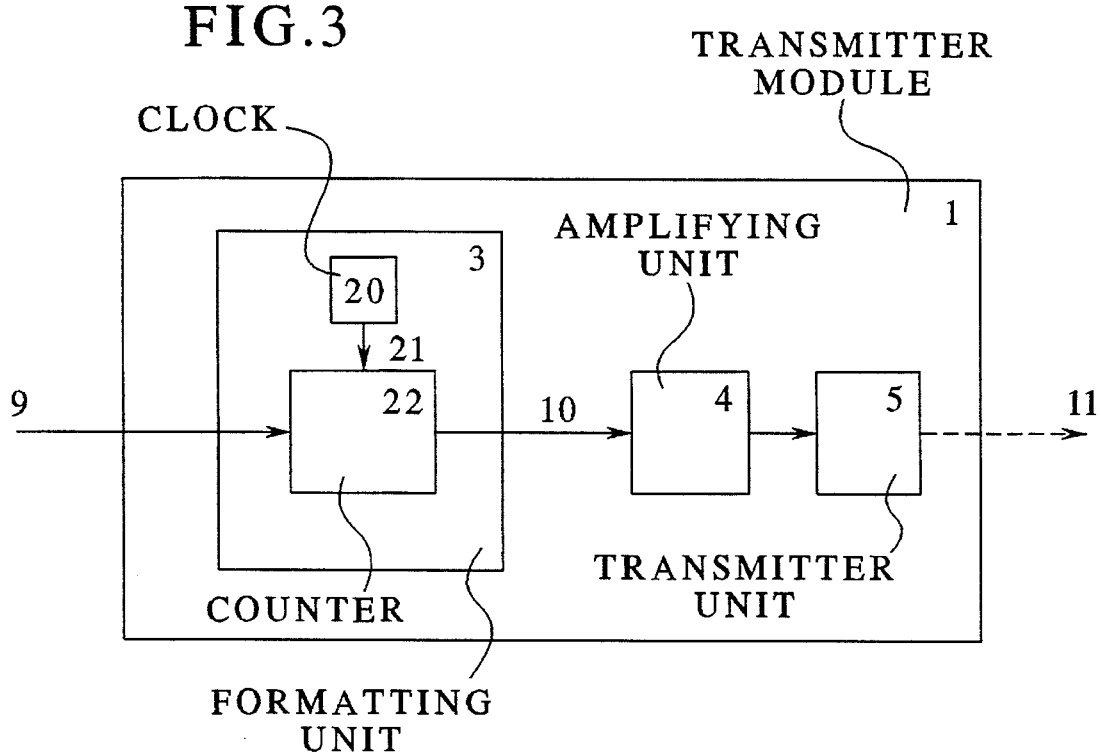
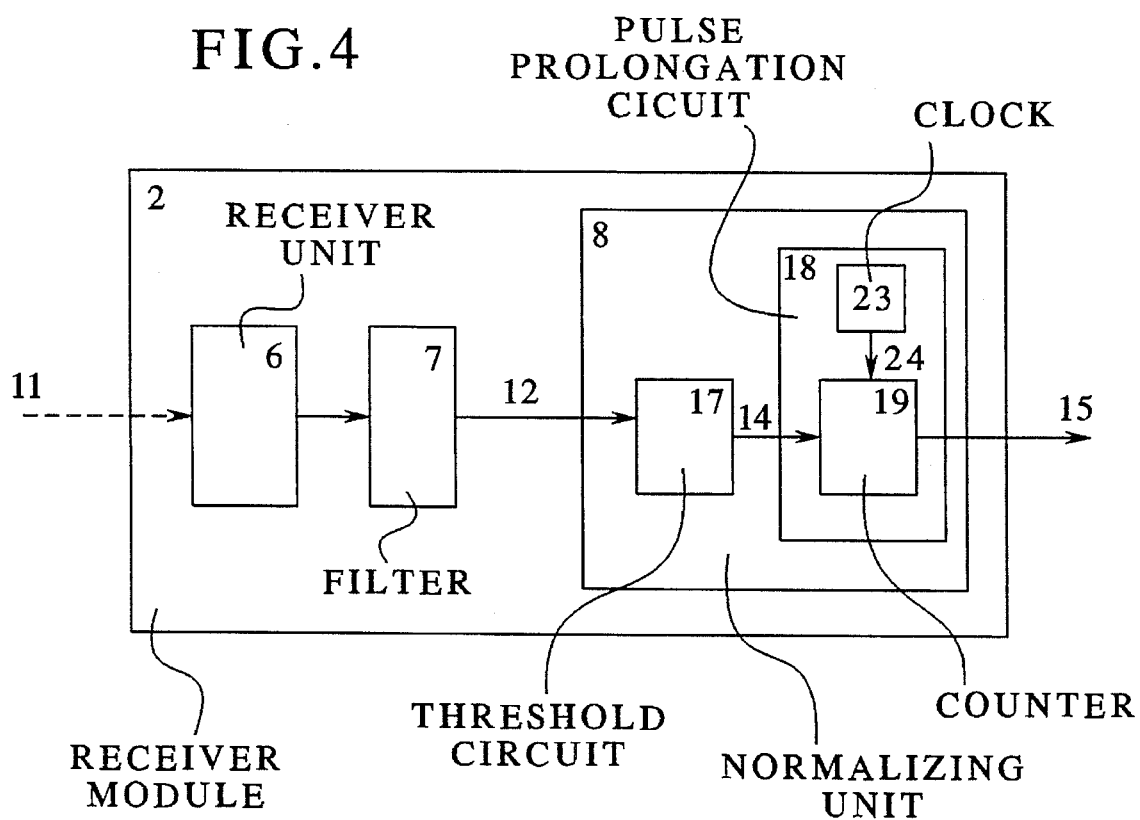

DEVICE FOR OPTICALLY TRANSMITTING AND RECEIVING BINARY INFORMATION

This is a continuation of application Ser. No. 08/401,236 filed Mar. 9, 1995 now abandoned.

BACKGROUND OF THE INVENTION

1. Field of the Invention

The present invention is directed to a device for optically transmitting binary information in a free medium between two or a number of units.

2. Description of the Prior Art

Non-galvanic transmission of information (i.e., transmission without the use of a direct path for electrical current between a transmitter and a receiver) can be employed in a plurality of fields for the transmission of digital information between units. One particular application is for transmissions between a medical implant's extracorporeal programmer and the programmer's base unit, e.g., a printer. Although a number of applications for the invention exist, e.g., in transmitting binary information between a printer and a computer or, generally, in transmitting binary information between mobile units without any galvanic contact between the units, it can be most easily understood and described in conjunction with one such application, i.e., a medical implant programmer, described below.

A programmer is an extracorporeal programming unit employed for programming a medical implant such as a pacemaker or an insulin pump. In the programming of the implant (exemplified below with a pacemaker), the programmer (or more accurately its telemetry coils), is applied to the patient's skin over the implant site in order to communicate with the implant by means of radio signals. Transmitted information can concern, e.g., a change in the pacemaker's stimulation interval or retrieval of ECG signals stored for diagnostic purposes in the pacemaker. The programmer communicates in turn with, e.g., a base unit when the programmer's software is to be updated and/or for downloading acquired information. The base unit comprises, e.g., a printer and a computer. Methods are currently known which make use of the programmer's telemetry coils both for the aforementioned telemetric transmissions to/from an implant and for communications between the programmer and the base unit. The amount of information which has to be transmitted between the programmer and base unit, however, is constantly increasing in step with the increasing complexity of contemporary pacemakers. For a programmer, several megabytes of information may have to be transmitted.

The transmission rate using telemetry coils for transmitting data between the programmer and base unit, however, is limited to a few thousand bits per second because, among other things, the time constants of the telemetry coils are relatively long. This results in unreasonably long transmission times being required when the programmer's telemetry coils have to transmit information in megabyte quantities. A significant increase in the transmission rate would therefore be desirable. Taking the programmer to the physician for pacemaker re-programming must also be easy, and therefore the programmer must be battery-powered. Low energy consumption is therefore an additional desirable feature.

British Specification GB 2 228 595 describes a device for optical transmission of digital information. This known device consists of a remote control unit which transmits signals to a receiver unit by means of, e.g., IR light. The signals are subjected to PPM which means that bursts of pulses are emitted at a specific interval between the first pulse in each pulse burst. The signal is modulated by varying the number of pulses in the burst of pulses.

In the known optical transmission described in this British Specification GB 2 228 595, communications are performed using a specific form of carrier wave modulation. One disadvantage with this kind of transmission art is that it consumes a relatively large mount of energy. Another disadvantage is that the transmission rate is not very fast.

U.S. Pat. No. 4,628,541 discloses an infra-red communications system for transmission of binary signals from a battery powered keyboard to a microcomputer. Each binary signal is transmitted from the keyboard to the microcomputer as a few (e.g., two or three) short infra-red pulses indicating the leading edge of the binary signal. Each binary bit ("1" or "0") to be transmitted is coded so that they can be distinguished from each other and then the infra-red generator is activated for the transmission. Since each bit to be transmitted is activating the generator, the system in U.S. Pat. No. 4,628,541 suffers the same disadvantages as the system of British Specification GB 2 228 595, namely it consumes a relatively large amount of energy and the transmission rate is not very fast.

European Application 0 585 030 discloses an infra-red transmission link between a base section and an external device, e.g. a handset. The bit-stream can be transmitted on the infra-red transmission path using binary amplitude modulation (ASK, Amplitude Shift Keying), in which the relative amplitude of the transmitted carrier is one for a transmitted −1-bit, and zero for a transmitted "0"- bit. The emitting frequency of the IR-LED can be used as the modulating carrier, whereby only the "1"-bits cause infra-red emission when the bit stream is transmitted. One "1"-bit can be transmitted as a short IR-pulse. The transmission system disclosed in European Application 0 585 030 is based on a mutual synchronization between a master-clock in the base section of the system and a clock generator in the handset. This synchronization of the clock generator in the handset is recovered from the transmitted bit-stream and requires special hardware, both in the base section and in the handset.

SUMMARY OF THE INVENTION

An object of the present invention is to achieve rapid, energy-saving transmission of binary information, thereby avoiding the disadvantages of the prior art.

The above object is achieved in accordance with the principles of the present invention in a device for optically transmitting binary information across a free medium includes means for generating a predetermined number of symbols, in the form of two information-carrying symbols with each information-carrying symbol having an associated symbol interval, and with one of the information-carrying symbols having a signal level which differs from zero, means for transmitting the information-carrying symbols optically via a free medium to a means for receiving the transmitted symbols. The means for transmitting may include an optical transmitter module having a transmitter unit which emits optical transmission signals comprising the aforementioned symbols, and the means for receiving may be in the form of an optical receiver module having a receiver unit for receiving the optical transmission signal. The device is made capable of asynchronous high-speed communication without a carrier wave by equipping the transmitter module with a formatting unit which activates the transmitter unit so as to emit the transmission signal only during a part of each complete symbol interval, and the receiver module includes a normalizing unit which recreates, from the received transmission signal, both the symbol corresponding to the transmission signal throughout its entire symbol interval, and the residual information-carrying symbol throughout its entire symbol interval.

As used herein, the term "free medium" means an open-unobstructed space, such as ambient atmosphere, which does not include obstructions which would block or otherwise significantly attenuate the transmission of the aforementioned signals, given the particular type of transmitter employed. Such a "free medium" includes or comprises a non-galvanic transmission path, as that term is described above.

According to one embodiment of the invention relating to a device for optical transmission of digital information in a free medium between two units, the device contains an optical transmitter module and an optical receiver module. According to other embodiments of the invention, an optical transmitter module and an optical receiver module are combined to form a joint unit. One such joint unit is located at a programmer for a medical implant and another such joint module is located in a base unit, such as a printer, for the programmer, permitting bi-directional communication between the programmer and its base unit.

in order to achieve rapid, energy-saving transmission of binary information (such as digital information) in the form of two information-carrying symbols each having an associated symbol interval, a transmitter unit, such as a light diode, in the transmitter module according to the invention is activated and emits a transmission signal only during the part of a complete symbol interval corresponding to one of the symbols. Activating the light-emitting diode only during part of the symbol interval eliminates the problems which occur at fast transmission rates for a transmission signal based on only one symbol, but in which the transmission signal is emitted throughout the entire interval. These problems are due to the fact that the time required to turn the light-emitting diode on and off becomes too long in relation to the duration of the symbol to be transmitted. This means, in combination with the time constants exhibited by, e.g., a photodiode at the receiver side, i.e., the time required for the photodiode to transform received light output into an electrical signal which is compared to a predetermined level, that the receiver has difficulty in determining the duration of the received signals. If, for example, two "ones" (a "one" designates an active light-emitting diode) are to be transmitted consecutively, the duration of the received signals determines the information it contains, and interpreting the received information as one or two "ones" can be difficult. In order to avoid these difficulties, the transmitting light-emitting diode is only activated during part of the symbol interval, e.g. the latter half, in accordance with the invention. The electrical signals generated by the light signals detected by the photodiode are compared, according to the invention, at the receiver side to a specific threshold value. If the signal exceeds this value, a light signal is deemed to have been received. Since the length of the symbol interval for the original signal is predetermined at the transmission side and at the receiver side, the original signal can be re-created from the received signal by prolongation of the received signal to one symbol interval. The mere detection at the receiver side that a signal has been received is therefore sufficient to reproduce the information content. The receiver does not have to determine the signal's duration.

Only activating the transmitter unit for one of the information-carrying symbols to be transmitted, and then only during part of the symbol interval, therefore achieves two things. The device consumes less energy, and a faster transmission rate is achieved with the device according to the invention than has heretofore been possible, since the limiting effects of the components are avoided.

DESCRIPTION OF THE DRAWINGS

FIG. 3 is a block diagram of the transmitter module of the device of the invention.

FIG. 4 is a block diagram of the receiver module of the device of the invention.

DESCRIPTION OF THE PREFERRED EMBODIMENTS

In the FIGS. 1–4, the same reference designations are used for similar or identical elements.

Figure 1:
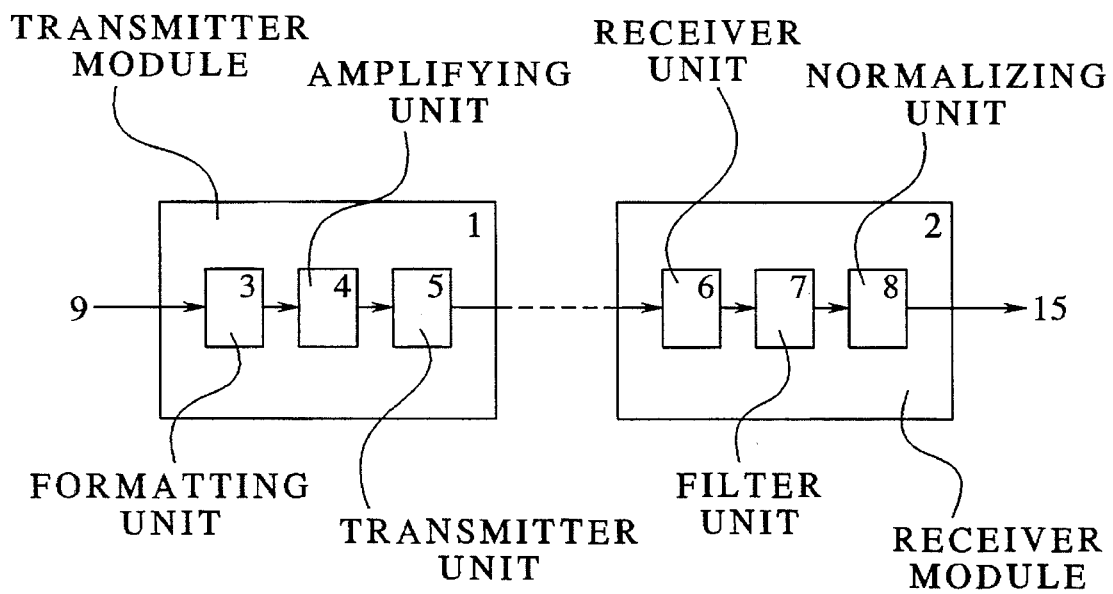
FIG. 1 is a block diagram of the device according to the invention.
Figure 2:
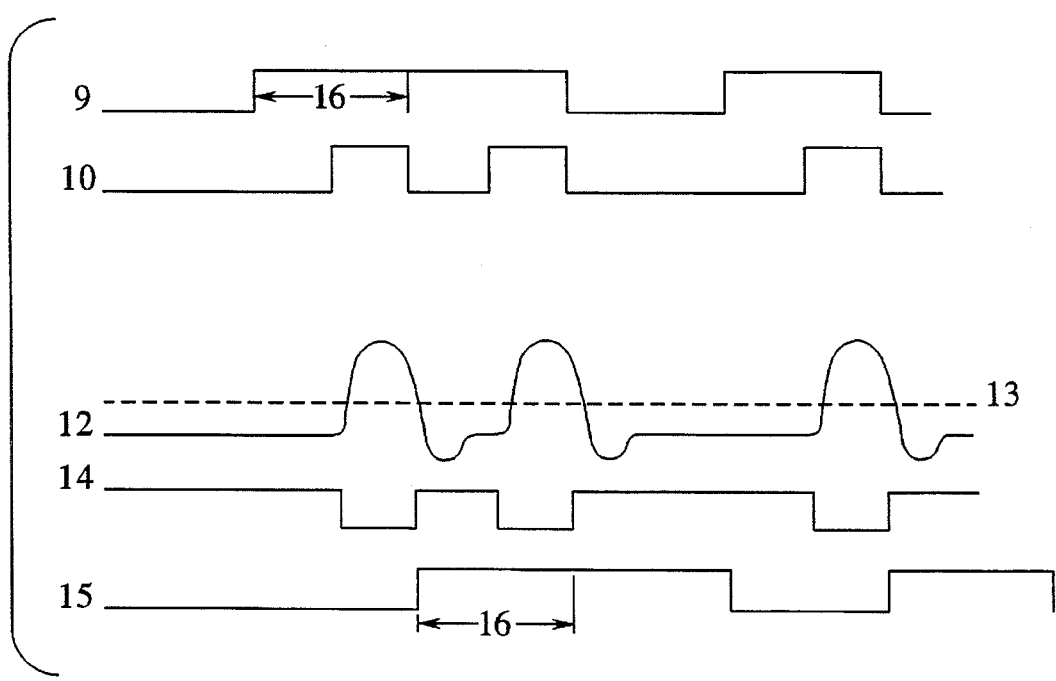
FIG. 2 shows, with horizontal time axes, different curve morphologies for a preferred embodiment of the device of the invention.

Referring to FIG. 1, a device for optical transmission of binary information at high speed in a free medium is shown which includes a transmitter module 1 and a receiver module 2. The transmitter module 1 contains a formatting unit 3, an amplifying unit 4 and a transmitter unit 5. The receiver module 2 contains a receiver unit 6, a filter unit 7 and a normalizing unit 8. FIG. 2 shows the morphology of the signals for different parts of the device of FIG. 1. Digital information 9 arriving at the transmitter module 1 is in the form of two information-carrying symbols, i.e., "ones" and "zeroes", each with an associated symbol interval 16 corresponding to a specific number of clock cycles from a first clock 20 (FIG. 3). In a preferred embodiment of the invention, the symbol interval corresponds to sixteen clock cycles. In the formatting unit 3, the binary information 9 is reformatted so a that formatted signal 10 is generated. After amplification in the amplifying unit 4, the formatted signal 10 activates the transmitter unit 5, causing it to emit a transmission signal 11 only during part of a complete signal interval 16 corresponding to one of the symbols. The transmitter unit 5 consists of a light-emitting diode (e.g., an IR diode, LED or laser diode) or some other light source, preferably an IR diode. The operation of the formatting unit 3 will be described in greater detail below.

The transmission signal 11 is detected by the receiver unit 6, preferably an IR photodiode, in the receiver module 2. The photodiode's weak electrical output signal is amplified and high-pass filtered in a filter unit 7 to eliminate low-frequency background signals with no information content, whereby a filtered signal 12 is generated which is sent to the normalizing unit 8 in which the filtered signal 12 is compared to a predetermined threshold value 13 (FIG. 2). If the filtered signal 12 exceeds this value, a transmission signal 11 has been received, and the normalizing unit 8 is devised to recreate both the symbol corresponding to the transmission signal 11 and the residual information-carrying symbol in the binary information 9.

The operation of the normalizing unit 8 will be described in greater detail below.

The operation of the formatting unit will first be explained, referring to FIGS. 2 and 3.

The formatting unit 3 contains a formatting counter 22 (which can be a "true" counter or an RC timer circuit), whose output terminal is connected to the amplifying unit 4, and a first clock 20 which generates a first clock signal 21 connected to the counter 22. Binary information 9 is sent to the input terminal of the counter 22, whereupon the formatted signal 10 generated by the counter 22 is high during part of a complete symbol interval 16 for one of the information-carrying symbols and low during the rest of that interval, whereas the formatted signal generated by the counter 22 is low for the other information-carrying symbol.

If activation of the transmitter unit 5 is desired during half of the symbol interval when the information-carrying symbol is a "one", a 50% duty cycle would thereby be used.

The optical transmitter module 1 operates according to return-to-zero (RZ) formatted, non-modulated signaling. This means that an output signal for an RZ-formatted circuit goes high for one of the data symbols in an arriving data signal for a predefined period of time and then returns to a low level. Non-modulation of the signal means that the resulting output signal has no carrier wave.

According to the preferred embodiment, binary information 9 is formatted by the formatting unit 3 into a 50% duty cycle, RZ form by clocking with the first clock 20, whose frequency is sixteen times faster than the frequency of the binary information 9. This is achieved when the formatted signal 10 generated by the counter 22 is low if the information-carrying symbol is a "zero". If the information-carrying symbol is a "one" the formatted signal 10 generated by the counter 22 is low for the first eight clock cycles and high for the next eight clock cycles. The formatted signal 10 is sent to the amplifying unit 4 and thereafter to the transmitter unit 5 which therefore emits the transmission signal 11 during the latter half of the symbol interval 16 when the information-carrying symbol is a "one".

The function of the normalizing unit 8 will now be described in greater detail, referring to FIGS. 2 and 4. The pulse prolongation circuit 18 in the normalizing circuit 8 contains a normalizing counter 19 (which can be a "true" counter or an RC time circuit) whose input terminal is connected to the output terminal of a threshold circuit 17. A second clock 23 which generates a second clock signal 24 is connected to the counter 19. A filtered signal 12 is obtained after amplification and high-pass filtering in the filter unit 7 of the transmission signal 11 received by the receiver unit 6. The filtered signal 12 is sent to the threshold circuit 17 which generates a threshold signal 14 which is normally high, but which is low during the time the filtered signal 12 exceeds a predetermined threshold value 13, whereupon the threshold signal 14 is sent to the normalizing counter 19. The positive-going leading edge of the threshold signal 14 at the return to a normally high level activates the counter 19 which emits an output signal 15 which is high for one symbol interval 16. This thereby recreates the symbol corresponding to the transmission signal 11 during the entire symbol interval 16.

According to an alternative construction, the threshold signal 14 is instead low in normal conditions but goes high when the filtered signal 12 exceeds the predetermined threshold value 13, whereupon the counter 19 is activated by the negative-going leading edge instead of the positive-going edge.

According to the preferred embodiment, the transmitter unit 5 is activated during the latter half of the symbol interval if the information-carrying symbol is a "one". The duration of a pulse of the threshold signal 14 can vary, depending on the level, of the transmission signal 11 received by the receiver unit 6, but the pulse duration corresponds to about half of the symbol interval 16. The positive-going edge of the threshold signal 14 activates a normalizing counter 19 in the pulse prolongation circuit 18, clocked by the same second clock 23 with the same frequency as at the transmitter side. The normalizing counter 19 emits an output signal 15 which is high for 16 clock cycles, corresponding to one symbol interval. This thereby recreates the original "one" in the binary information 9.

When the transmitter module 1 is to transmit binary information to the receiver module 2, the transmitter module 1 begins transmitting immediately. The receiver module 2 is always ready to detect the transmission signal. Transmission of binary information 9 always commences with a start bit which is one of the information-carrying symbols and always ends with a stop bit which is the other information-carrying symbol. Thus, transmission always comprises a predetermined number of information-carrying symbols between the start bit and the stop bit.

Memory units, buffer units and control means are arranged in the formatting unit 3 and in the normalizing unit 8. The protocol used for transmitting the binary information is specified therein, e.g. the predetermined number of information-carrying symbols and the morphology of the start and stop bits are specified. The binary information can be stored in buffers before formatting in the transmitter module 1 and after normalization in the receiver module 2.

One of the information-carrying symbols can be recreated when a transmission signal 11 has been received by the receiver module 2. When no transmission signal 11 is received between a start bit and a stop bit during a transmission session, this represents the second information-carrying symbol, or residual information-carrying symbol, in the original binary information. Thus, the output signal emitted by the normalizing unit 8 consists of the recreated binary information.

The transmission rate for the preferred embodiment of the device is 230400 baud, corresponding to a symbol interval of bout 4.3 µs.

One special application of the invention is in the context of an extracorporeal programmer for a medical implant. The programmer and its base unit each contain a device for high speed optical transmission of digital information in a free medium. The device has both an optical transmitter module and an optical receiver module forming a joint unit. One joint unit is arranged at the programmer and another at the base unit. Duplex (simultaneous bi-directional) transmission of binary information between the programmer and the base unit is possible when the programmer is placed at the base unit in such a position that the respective transmitter and receiver modules of the joint units are opposite one another.

Another application of the invention is to have the transmitter module communicate with a plurality of receiver modules, or vice-versa.

Although modifications and changes may be suggested by those skilled in the art, it is the intention of the inventor to embody within the patent warranted hereon all changes and modifications as reasonably and properly come within the scope of his contribution to the art.

I claim as my invention:

1. A device for transmitting and receiving binary information, said binary information comprising a predetermined number of symbols, each assuming the form of either one of two information-carrying symbols dependent on its information content, each information-carrying symbol having an associated symbol interval, and one of said information-carrying symbols having a signal level differing from zero, said device comprising:

transmitter means for optically transmitting a transmission signal containing said binary information via a free medium without a carrier wave, said transmitter means including an on/off transmission element and means for driving said on/off transmission element at a high transmission rate;

formatting means, connected to said transmitter means, for activating said on/off transmission element of said transmitter means only once per symbol interval to continuously emit said transmission signal, the information-carrying symbol having a signal level differing from zero only during a part of said symbol interval;

receiver means for optically receiving said transmission signal via said free medium; and normalizing means, connected to said receiver means, for recreating, from the transmission signal received by said receiver means, both a symbol corresponding to the transmission signal having a signal level differing from zero throughout its symbol interval and an information-carrying symbol having a signal level not differing from zero throughout its symbol interval in said binary information.

2. A device as claimed in claim 1 wherein said formatting means generates a formatted signal, and further comprising amplifier means, connected between said formatting means and said transmitter means, for amplifying said formatted signal for activating said transmitter means.

3. A device as claimed in claim 1 further comprising filter means, connected between said receiver means and said normalizing means, for filtering said transmission signal.

4. A device as claimed in claim 1 wherein said transmitter means comprises a light-emitting diode and wherein said receiver means comprises a photodiode.

5. A device as claimed in claim 1 wherein said normalizing means comprises:

threshold means, supplied with said transmission signal received by said receiver means, for normally generating a threshold output signal at a first level and for generating a threshold output signal at a second level for a time during which said transmission signal from said receiver means exceeds a predetermined threshold level; and counter means, supplied with said threshold output signal, for emitting a counter output signal, beginning at a leading edge of said threshold output signal, which is at said first level during one symbol interval for recreating said symbol from said transmission signal throughout its entire symbol interval.

6. A device as claimed in claim 1 wherein said formatting means generates a formatted signal, and wherein said formatting means comprises counter means, having an input supplied with said transmission signal and an output at which said formatted signal is emitted, for generating said formatted signal as a signal which is high only during a part of a complete symbol interval for a first of said information-carrying symbols and which is low for a second of said information-carrying symbols, said counter means starting with a start bit which is always one of said information-carrying symbols having a signal level differing from zero and ending with a stop bit which is always the other information-carrying symbol.

7. A transmitter module for transmitting binary information, said binary information comprising a predetermined number of symbols, each assuming the form of either one of two information-carrying symbols dependent on its information content, each information-carrying symbol having an associated symbol interval, and one of said information-carrying symbols having a signal level differing from zero, said transmitter module comprising:

transmitter means for optical transmitting a transmission signal containing said binary information via a free medium without a carrier wave, said transmitter means including an on/off transmission element and means for driving said on/off transmission element at a high transmission rate; and formatting means, connected to said transmitter means, for activating said on/off transmission element of said transmitter means only once per symbol interval to continuously emit said transmission signal, the information-carrying symbol having a signal level differing from zero only during a part of said symbol interval.

8. A transmitter module as claimed in claim 7 wherein said formatting means generates a formatted signal, and further comprising amplifier means, connected between said formatting means and said transmitter means, for amplifying said formatted signal for activating said transmitter means.

9. A transmitter module as claimed in claim 7 wherein said formatting means generates a formatted signal, and wherein said formatting means comprises counter means, having an input supplied with said transmission signal and an output at which said formatted signal is emitted, for generating said formatted signal as a signal which is high only during a part of a complete symbol interval for a first of said information-carrying symbols and which is low for a second of said information-carrying symbols, said counter means starting with a start bit which is always one of said information-carrying symbols having a signal level differing from zero and ending with a stop bit which is always the other information-carrying symbol.

* * * * *